United States Patent [19]

Miksch

[11] Patent Number: 4,790,857
[45] Date of Patent: Dec. 13, 1988

[54] GASEOUS CONTAMINANT DOSIMETER WITH DIFFUSIVE MATERIAL FOR REGULATING MASS UPTAKE

[76] Inventor: Robert R. Miksch, 548 E. Mallard Cir., Fresno, Calif. 93710

[21] Appl. No.: 932,940

[22] Filed: Nov. 20, 1986

[51] Int. Cl.⁴ .............................................. B01D 53/22
[52] U.S. Cl. ............................................ 55/16; 55/158; 55/270; 73/863.21; 73/864.51; 422/61; 422/86; 422/88; 422/101; 436/178; 436/902
[58] Field of Search ............................. 55/158, 16, 270; 422/59, 61, 86, 88, 101, 102; 436/167, 168, 178, 902; 73/863.21, 864.51

[56] References Cited

U.S. PATENT DOCUMENTS

| | | |
|---|---|---|
| 1,252,975 | 1/1918 | Webster . |
| 2,958,391 | 11/1960 | De Rosset .......................... 55/158 X |
| 3,223,487 | 12/1965 | Grosskopf . |
| 3,415,038 | 12/1968 | Merten et al. ...................... 55/158 X |
| 3,784,358 | 1/1974 | Drake, Jr. . |
| 3,924,219 | 12/1975 | Braun . |
| 3,945,798 | 3/1976 | Young . |
| 3,950,980 | 4/1976 | Braun et al. . |
| 3,985,017 | 10/1976 | Goldsmith ............................ 73/23 X |
| 4,040,805 | 8/1977 | Nelms et al. ......................... 55/158 |
| 4,102,201 | 7/1978 | Trine et al. . |
| 4,157,960 | 6/1979 | Chang et al. ....................... 55/16 X |
| 4,158,958 | 6/1979 | Braun ................................. 422/88 X |
| 4,159,304 | 6/1979 | Shono . |
| 4,205,043 | 5/1980 | Esch et al. . |
| 4,208,371 | 6/1980 | Kring . |
| 4,235,097 | 11/1980 | Kring et al. . |
| 4,265,635 | 5/1981 | Kring . |
| 4,267,023 | 5/1981 | Frant et al. ....................... 436/902 X |
| 4,324,632 | 4/1982 | Tantram et al. ................... 204/415 |
| 4,326,200 | 4/1982 | Bushman . |
| 4,349,356 | 9/1982 | Wakao ................................. 55/16 |
| 4,350,037 | 9/1982 | Higham . |
| 4,380,587 | 4/1983 | Koocher . |
| 4,393,113 | 7/1983 | Sugie et al. ....................... 55/158 X |
| 4,428,907 | 1/1984 | Heijenga et al. . |
| 4,436,819 | 3/1984 | Manning ........................... 436/902 X |
| 4,444,662 | 4/1984 | Conover ............................ 55/158 X |
| 4,583,996 | 4/1986 | Sakata et al. ...................... 55/158 X |

FOREIGN PATENT DOCUMENTS 1075054 7/1967 United Kingdom .

Primary Examiner—Kathleen J. Prunner
Attorney, Agent, or Firm—Worrel & Worrel

[57] ABSTRACT

A gaseous contaminant dosimeter apparatus for collecting, for subsequent analysis, a gaseous contaminant in proportion to its average concentration in the ambient atmosphere over a predetermined collection period. The gaseous contaminant dosimeter apparatus includes a closed chamber containing a medium capable of chemically or physically combining with the selected gaseous contaminant, and porous diffusive material formed from a material through which the contaminant may diffuse at a rate that is proportional to its atmospheric concentration and substantially unaffected by convective movements of the ambient atmosphere, is mounted in fluid impeding relation with the chamber. The diffusive material includes at least two layers of microporous membrane material having a multiplicity of pores which individually have effective cross-sectional dimensions that are smaller than the mean free path length of the contaminant, the membrane material being mounted on the opposite sides of a porous support substrate.

9 Claims, 1 Drawing Sheet

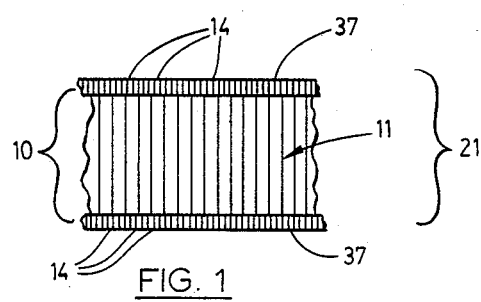
FIG. 1
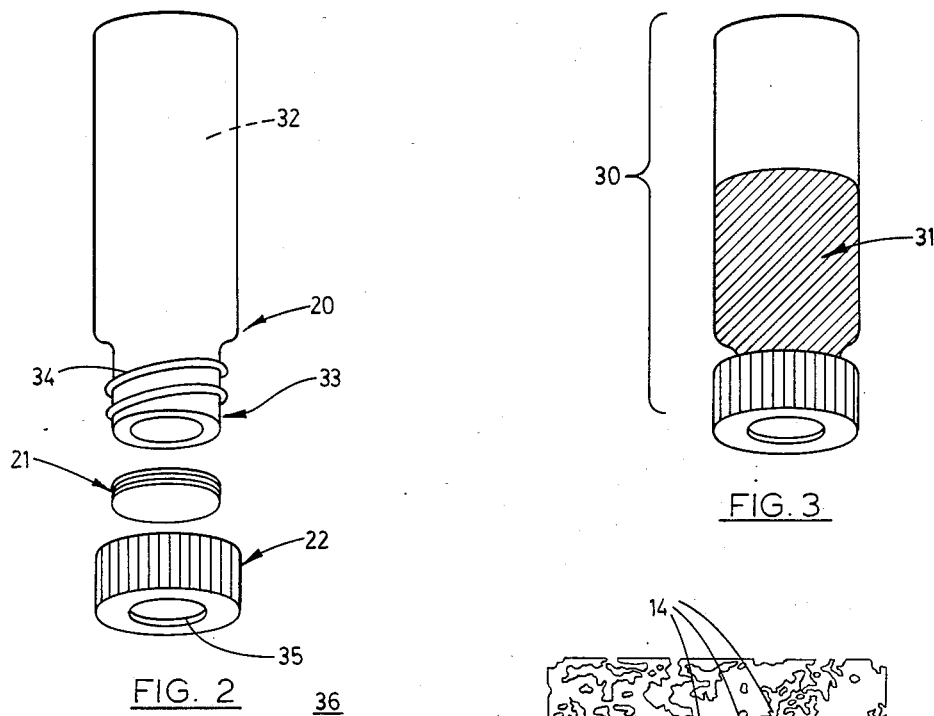
FIG. 2
FIG. 3
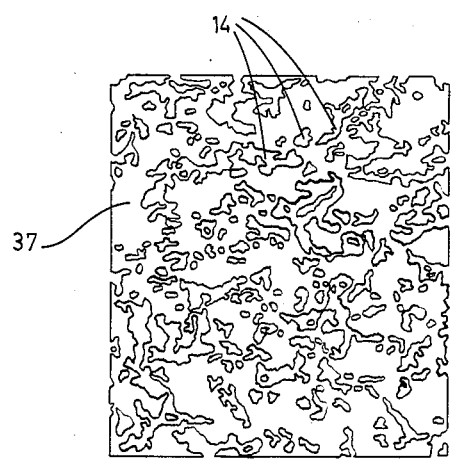
FIG. 4

GASEOUS CONTAMINANT DOSIMETER WITH DIFFUSIVE MATERIAL FOR REGULATING MASS UPTAKE

BACKGROUND OF THE INVENTION

1. Field of the Invention

The present invention relates generally to the fabrication of a dosimeter which is operable to measure the time-weighted concentration of one or more gaseous contaminants in an ambient atmosphere, and more specifically to the selection of particular starting materials, and the fabrication of a diffusive material which permits the passage of a selected gas or gases in a gas mixture solely by a diffusive mechanism in proportion to a concentration gradient of the selected gas or gases across the same diffusive material and independent of the convective movement of the impinging gas mixture. The subject diffusive material adapted to be manufactured in continuous sheets and thereafter formed into any desired sizes or shapes.

2. Description of the Prior Art

The prior art is replete with numerous examples of sampling apparatuses which are operable to detect a wide range of gaseous contaminants in assorted operational environments. For example, in the field of monitoring gaseous contaminants which may reside from time to time in the ambient atmosphere, much of the recent art has been directed towards constructing dosimeters which employ passive means to regulate mass transfer of the particular gaseous contaminant to be detected between the ambient atmosphere containing same and a selected collection medium, thereby eliminating the need for an active pump. Such passive dosimeters typically have operational characteristics which include no moving parts, can be fabricated inexpensively, are simple to utilize, and can be easily affixed to employees for purposes of making personal "breathing zone" measurements. These "breathing zone" measurements permit a more accurate risk assessment to be conducted than what was heretofore possible with the more traditional fixed-site area measurements performed with more elaborate or technologically cumbersome instrumentation.

The authors, Palmes and Gunnison in an article entitled "Personal Monitoring Device for Gaseous Contaminants," American Industrial Hygiene Association Journal, 34, 78–81 (1973) disclosed such a passive dosimeter which measured concentrations of a selected gas by measuring the quantity of the gas which diffused through a single orifice of known size to a collection element, where the concentration of the selected gas was maintained at zero.

Although substantial prior art exists, all passive dosimeters disclosed heretofore have utilized one of only two basic mass transport mechanisms thereby achieving the desired objective of regulated mass transfer. These basic mass transport mechanisms include permeation which takes place through a solid polymeric membrane, and bulk gas diffusion.

Passive dosimeters which employ the mass transport mechanism of permeation typically are configured in a form wherein a solid polymeric membrane is disposed in an attitude between an ambient atmosphere containing a gaseous contaminant to be detected and a collection medium for same. As should be understood, the gaseous contaminant "dissolves" in the solid polymeric membrane and mass uptake occurs when a concentration gradient is established across this same polymeric membrane. The concentration gradient is created, of course, when the collection medium adsorbs or absorbs as appropriate, the contaminant in question. Under steady-state conditions the amount of material which will typically pass into a passive dosimeter in a given time "t" is illustrated by the formula:

$$W = kA(C_a - C_i)t/L \tag{1}$$

where $W$ = the weight of the material collected expressed in micrograms; $k$ = the empirically determined permeation coefficient expressed in square centimeters per minute; $A$ = the area of the permeation membrane exposed expressed in square centimeters; $C_a$ = the concentration of gaseous contaminant in the ambient atmosphere to be tested expressed in micrograms per cubic centimeter; $C_i$ = the concentration of the gaseous contaminant contained inside the dosimeter (normally zero provided that an efficient collection medium is used); $t$ = the time of sampling expressed in minutes; and $L$ = the length (thickness) of the permeation membrane which is expressed in centimeters. Values of k for polymeric silicon membranes, which are considered the most permeable, and therefore preferred, as disclosed in the reference authored by K. D. Reizner and P. W. West entitled "Collection and Determination of Sulfur Dioxide Incorporating Permeation and West-Gaeke Procedure," Environmental Science and Technology, 7, 526–532 (1973) are indicated as lying in a range between 0.001 and 0.01 square centimeters per minute.

Passive dosimeters which employ the mass transport mechanism of permeation have three major advantages. Firstly mass uptake by the mechanism of permeation which takes place through a solid polymeric membrane appears to be substantially resistant to disturbance occasioned by the variable convective movements of the surrounding ambient atmosphere which are normally encountered during most sampling applications, and therefore no secondary protective design features need be employed. Secondly, the utilization of a solid permeation membrane has the attendant characteristic of being capable of retaining solid or liquid collection media, again without the incorporation of secondary design features. Thirdly, a permeation membrane may be manufactured as a sheet of substantially continuous material therefore allowing considerable latitude with respect to the area and shape of material to be incorporated into a dosimeter.

While the previous prior art devices and practices have achieved numerous laudable benefits, they have a multiplicity of shortcomings which have detracted from their usefulness. For example, dosimeters employing the mass transport mechanisms of permeation have several major drawbacks: (1) The rate of mass uptake, by permeation, must be empirically determined for each selected gaseous contaminant to be detected and frequently for each individual dosimeter because gas "solubilities" cannot in reality accurately be predicted from theory and may vary widely even within single lots of commercially available membrane; (2) very thin and often fragile membranes must be employed to achieve practical sampling rates; (3) the time required to achieve an equilibrium rate of mass uptake can be relatively long as compared with the concentration fluctuations of the gas contaminant to be detected in the ambient atmosphere, hence the contaminant sample collected may not accurately reflect the time-weighted average measure; and (4) the rate of mass uptake may be adversely affected by changes in the temperature or ambient humidity. These several shortcomings have heretofore frequently offset the benefits derived from employing permeation dosimeters, and as a result the preponderance of passive dosimeters now being utilized are of the bulk diffusion type.

It should be understood that the passive dosimeters disclosed to date have generally incorporated one or more substantially still pockets of air which individually have macroscopic dimensions relative to the mean free path length of the gaseous contaminant to be detected, and which is placed between the ambient atmosphere to be sampled, and the selected collection medium. The contaminant is collected according to Fick's First Law of Diffusion which is set forth below:

$$W = pD_b A(C_a - C_i)t/L \qquad (2)$$

where W=the weight of the material collected expressed in micrograms; p=the porosity of the material through which the gas contaminant is diffusing (the fractional void volume, which is generally accepted as being equal to one (1) in an open system); $D_b$=the bulk gas diffusion coefficient expressed in square centimeters per minute; A=the area of the permeation membrane exposed expressed in square centimeters; $C_a$=the concentration of the gaseous contaminant contained in the ambient atmosphere expressed in micrograms per cubic centimeter; $C_i$=the concentration of the gaseous contaminant contained inside the dosimeter (this being normally zero, provided of course, that an efficient collection medium is used); t=the time of sampling expressed in minutes; and L=the length (thickness) of the permeation membrane expressed centimeters. It has been empirically determined that the bulk gas diffusion coefficients for molecules with molecular weights of 300 or less which diffuse through the air lie in a range between 3 and 10 square centimeters per minute under ambient temperature and pressure conditions. It should be understood that molecules with molecular weights of 300 or less are most likely to have a measurable vapor pressure.

Gaseous dosimeters that employ the mass transport mechanism of bulk diffusion to regulate mass uptake of a selected contaminant have several noteworthy advantages. Firstly, dosimeter performance can be accurately predicted from theory by simply substituting diffusion coefficients derived from experiment or theory into equation (2) which was discussed above; Secondly, intra- and inter-dosimeter sampling rates are substantially precise because of the ability to accurately form bulk diffusion channels of substantially uniform dimension; thirdly, the rate of mass transfer is substantially independent of the effects of pressure and humidity and will generally vary with temperature only to an amount expressed as $T^{\frac{1}{2}}$; and fourthly, the time required to achieve an equilibrium rate of mass uptake typically is rapid as compared to the concentration fluctuations of the gas contaminant in the immediate ambient atmosphere to be tested.

The disadvantages which are attendant with the utilization of bulk diffusion dosimeters are a result of shortcomings inherent in their respective designs. For example, bulk diffusion dosimeters need to incorporate secondary design features to prevent convective air movement, which takes place adjacent to the dosimeter, from disrupting the still pocket of air necessary to regulate mass uptake, and to retain the collection media which might otherwise be released through an open diffusion channel which is generally present in such devices. Two approaches have been utilized to overcome the above noted shortcomings. The first approach has been to employ one or more substantially circular diffusion channels which are individually closed at one end by the collection medium and which further have a ratio of length-to-diameter which exceeds a minimum valve of three. U.S. Pat. No. 4,235,097 and an article authored by W. J. Lautenberger, E. V. Kring, and J. A. Morello entitled "A new personal badge monitor for organic vapors" found in the American Industrial Hygiene Association Journal, 41 737-747 (1980); and the article written by R. H. Brown, J. Charlton, and K. J. Saunders, entitled "The development of an improved diffusive sampler," American Industrial Hygiene Association Journal, 42, 865-869 (1981); discuss this principal in greater detail. In practice, however, ratios of ten or greater are commonly required to satisfactorily attenuate the deleterious effects of convective air movements thereby leading to disadvantageously reduced sampling rates. The second approach is to utilize a sheet of substantially macroporous material as a "wind screen." For example, U.S. Pat. No. 3,950,980 to Brown et al. discloses the use of two or more layers of porous material having effective pore sizes in a range between 0.1 and 100 micrometers which are used to attenuate convective gas movement so as to create one or more thin layers of placid gas within an enclosure. Further, U.S. Pat. No. 3,985,017 to Goldsmith discloses the use of a porous sheet having preferred effective pore sizes in an effective range between 5 and 50 micrometers that permits unhindered diffusion, and which is disposed in an attitude at the entrance of an enclosure containing an internal honeycomb structure that substantially inhibits convective movement. It should be appreciated, however, that the latter problem has been most often addressed by utilizing a self-supporting or otherwise solid collection medium, although parenthetically it should be noted that U.S. Pat. No. 4,265,635 discloses the use of a porous hydrophobic film (50-80% porous having pore sizes in the range of 0.1-3.0 micrometers) placed over the end of a plurality of diffusive channels and operable not to interfere with the passage of gaseous contaminants between the ambient air to be tested and a liquid collection medium.

Therefore, it has long been known that it would be desirable to have a gaseous contaminant dosimeter that can incorporate the performance and design features of both permeation and bulk diffusion type dosimeters while simultaneously avoiding the detriments individually associated therewith, and which further is particularly well suited to being transported easily by employees, can be manufactured in a compact configuration and which is operable to provide accurate concentration measurements for the gaseous contaminants to be detected.

SUMMARY OF THE INVENTION

Therefore, it is an objective of the present invention to provide an improved gaseous contaminant dosimeter.

Another objective of the present invention is to fabricate a diffusive material which can be produced in continuous sheets, is substantially self-protecting against the deleterious effects of convective air movement, and which further is capable of containing either a solid or a liquid collection medium in the fashion of solid permeation membranes.

Another objective of the present invention is to fabricate a diffusive material that has a high rate of mass transfer and exhibits uniform performance characteristics when fabricated in quantity.

Another objective of the present invention is to provide a diffusive material which has performance properties which are predictable based on theory and/or a minimum of empirical data, is rapidly responsive to gas contaminant concentration fluctuations, and which further exhibits a small or otherwise predictable dependence upon environmental variables in the manner of bulk diffusion.

Another objective of the present invention is to construct an inexpensive and versatile passive dosimeter using a source of continuously fabricated diffusive material.

Another objective of the present invention is to provide a diffusive material that regulates mass uptake of a gas contaminant to be detected in a gas mixture, most commonly air, by a collection medium, at a rate which is proportional to the gaseous concentration of the contaminant and substantially unaffected by the convective movement of the entraining gas mixture.

Another objective of the present invention is to provide a diffusive material which takes on the form of a laminate and which has two substantially identical outwardly disposed sheets of microporous PTFE membrane, the individual membranes having a predominance of pores with effective cross-sectional dimensions which are smaller than the mean free path length of the gaseous contaminant in the ambient atmosphere, and larger than the molecular size of the same contaminant, the individual membranes bound to the opposite sides of a macroporous polyethylene core.

Another object of the present invention is to provide a diffusive material wherein the majority of the resistance to mass uptake is exhibited by the collection medium and is confined to the outer microporous layer of PTFE, the resistance to mass uptake substantially governed by the elastic collisions of the gas contaminant molecules with the pore walls.

Another object of the present invention is to provide an improved gaseous dosimeter wherein mass transfer takes place in accordance with "Knudsen regime" diffusion theory, said mass transfer being proportional to the concentration gradient created across the diffusive material as the collection medium adsorbs or absorbs the contaminant as appropriate, and further is inherently resistant to disturbance from convective air currents in the immediate vicinity of the dosimeter.

Another object of the present invention is to provide an improved dosimeter wherein solid or aqueous solution collecting media can be retained by the diffusive material with the latter substantially prevented from penetrating same by the hydrophobic properties exhibited by PTFE.

These and other objects and advantages are achieved in the apparatus of the instant invention wherein there is provided an improved gaseous contaminant dosimeter that is operable to collect, for subsequent analysis, a selected gaseous contaminant in proportion to its average concentration in the ambient atmosphere during the collection period, and which includes a glass vial containing either a liquid or solid collection medium, the glass vial having an open end which is sealed by a piece of diffusive material that is held in place by a threaded cap which has an orifice formed therein; communication between the gaseous contaminant in the ambient atmosphere and the collection medium taking place through the piece of diffusive material.

BRIEF DESCRIPTION OF THE DRAWINGS

FIG. 1 is a somewhat enlarged transverse sectional view of the diffusive material of the instant invention showing the construction of the sheet of diffusive material.

FIG. 2 is a perspective exploded view of the gaseous contaminant dosimeter of the instant invention.

FIG. 3 is an illustrative perspective view of the gaseous contaminant dosimeter in a preferred orientation which places an aqueous collection medium in contact with the disk of diffusive material.

FIG. 4 is a plan view of the diffusive material of the instant invention and showing the microscopic internal free passage structure of a representative sample of the same diffusive material.

DESCRIPTION OF THE PREFERRED EMBODIMENT

Referring more particularly to the drawings, the apparatus of the subject invention is best understood by a study of FIG. 1. As shown therein, a container or vial generally indicated by the numeral 20 defines a void 32 and has a neck 33 which has formed therein a raised thread 34 that is operable screw-threadably to mate with a cap generally indicated by the numeral 22. The cap 22 has an orifice or opening 35 formed therein which permits fluid flow communication between the ambient atmosphere 36 and the void 32. The cap further is operable to secure a piece of appropriately dimensioned diffusive material 21 in fluid impeding relation in the neck 33 of the container 20.

As should be understood, the fabrication of a diffusive material 21 that would meet the objectives of the invention begins with a consideration of the properties of microporous PTFE membranes 37. Those skilled in the art will readily recognize that PTFE is marketed under the trademark Teflon ® by E. I. Dupont Co. Manufacturer's data provided by W. M. Gore & Associates for typical PTFE membranes 37, are set forth in TABLE 1 and show that resistance to air and water permeation in response to a pressure gradient across a PTFE membrane of selected pore size is inversely related to the pore size. After due consideration of the problems related to physically providing support for the PTFE membranes, the need to resist convective air movement at the exterior surface of the diffusive material 21, the desirability of preventing a source of aqueous collection media 31 from penetrating through the diffusive material, and the objective of fabricating a simple dosimeter whereby a decision would not have to be made by field personnel concerning the proper orientation of the diffusive material in the neck 33 of the container 20, the symmetrical laminate structure, which is best shown in FIG. 1, was selected. The manufacturer of the PTFE membranes shown in TABLE 1 provided four experimental laminates wherein PTFE membranes having individual pore sizes of 0.02, 0.2, 1.0 and 10 micrometers, respectively, were thermally bound in a fashion so as to preserve their microporous characteristics, to both sides of a 1/16" thick (1.588 mm.) rigid sheet of substantially porous (50% void volume) polyethylene. This was done in order to investigate the relationship of the pore sizes and the abilities of the individual PTFE membranes 37 to resist convective air movement and to retain the aqueous collection media 31. As should be understood, manufacturers of PTFE membranes 37 employ a "bubble point test" to determine the pore size of the respective membranes. During the bubble point test, pressure is applied to a wetted membrane for purposes of blowing bubbles. This relationship of pressure with the production of bubbles is thereafter correlated and the appropriate pore size is assigned to the PTFE membrane.

TABLE 1

| Pore Size | Thickness | Void Volume | Air Flow Rate (1) | Minimum Water Entry Pressure |
|---|---|---|---|---|
| 0.02 μm | 0.003 inches | 50% | 3 mL/min-cm² | 350 PSI |
| 0.2 | 0.0025 | 78 | 75 | 40 |
| 0.45 | 0.003 | 84 | 170 | 20 |
| 1.0 | 0.003 | 91 | 530 | 10 |
| 3 | 0.001 | 95 | 1200 | 2 |
| 5 | 0.001 | 95 | 5700 | 0.5 |
| 10–15 | 0.0005 | 98 | 14600 | 0.25 |

(1) Measured at a pressure drop of 4.88" of water.

The gaseous contaminant dosimeters of the instant invention, which are generally indicated by the numeral 30, were constructed of the design which is best illustrated by reference to FIGS. 2 and 3. As shown in FIG. 3 the dosimeter 30 includes a clear glass vial 20 having a void 32 of a capacity of approximately 16 mL. The void 32 receives an aliquot of aqueous collection media 31. As earlier discussed the cap 22 is adapted to retain a disk of diffusion material 21 is fluid impeding relation in the neck 33. The cap further is operable to exert sufficient force on the diffusive material to prevent the seepage of the collection media from around the edges of same when the dosimeter 30 is placed in the preferred inverted orientation shown in FIG. 3 thereby bringing the collection medium into contact with the diffusive material 21. The rigid core 11, of the diffusive material, maintains the relative dimensional stability of same while it is retained by the cap in an appropriate fluid impeding relationship in the neck 33. When appropriately assembled the only communication between a gas contaminant (not shown) in the ambient atmosphere 36 and the collection medium 31 is through the diffusive material 21.

The abilities of the experimental laminates or diffusive material 21 to resist convective air movement and simultaneously retain a predetermined volume of aqueous collection medium 31 were tested in a series of experiments wherein the gaseous contaminant dosimeters 30 were threaded into open top caps which had been affixed to perforations in a tubular manifold, not shown, and in such a fashion that the exterior surface of the diffusive material to be tested was presented to the inside portion of the manifold. The aqueous collection medium 31 was placed in each dosimeter 30 and a test atmosphere containing a gas contaminant was passed through the manifold under essentially laminar conditions at linear velocities between 50 and 280 feet per minute (fpm), a range encompassing the average velocity of convective air movement encountered during personal sampling (National Institute of Occupational Health and Safety Contract No. 210-78-0115-0000). The results obtained from this experimental inquiry are shown in TABLE 2.

TABLE 2

| | Sampling Rate (cm³/min) at Given Face Velocity (1) | | | |
|---|---|---|---|---|
| Membrane Pore Size | 50 fpm | 100 fpm | 200 fpm | 280 fpm |
| 0.02 | 7.8 | 8.2 | 7.8 | 8.8 |
| 0.2 | 13.9 | 14.8 | 21.4 | 28.7 |
| 1.0 | 24.0 | 29.7 | 46.3 | 61.5 |
| 10 | 34.7 | 39.3 | 55.9 | 60.3 |
| theoretical sampling rate for pure bulk diffusion | | | 31.6 | |

The dosimeters 30 contained a collection medium 31 consisting of 5 mL of a 0.05% aqueous solution of 3-methyl-2-benzothiazolone hydrazine hydrochloride (MBTH) and were exposed to a test atmosphere of approximately 0.3 parts per million (ppm) formaldehyde (1/10th of the level allowed by the Occupational Health and Safety Administration for workers) for a period of approximately 4 hours. After exposure to the contaminants an oxidizing reagent consisting of ferric chloride and sulfamic acid was added to each dosimeter to produce a color which was later quantified by utilizing a spectrophotometer. The aforementioned method is the one recommended by the American Public Health Association (Method 117, Tentative Method of Analysis for Formaldehyde Content of the Atmosphere (MBTH-Colorimetric Method-Application to Other Aldehydes, pp 308-313 in Methods of Air Sampling and Analysis, APHA Intersociety Committee, Washington, D.C.).

The test results summarized in TABLE 2 indicated that all of the diffusive materials 21 could retain the aqueous collection media 31 under quiescent experimental conditions. However, the diffusive material constructed from 10 micron pore size PTFE membranes 37 could not retain the collection media when subjected to mild agitation similar to that which would normally be experienced during personnel sampling. Of the three remaining test diffusive materials only the one fabricated from PTFE membrane of the smallest pore size, that is 0.02 microns, successfully resisted convective air movement and provided a regulated rate of mass transfer. Further, it was observed that the rate of mass transfer was lower than what would be predicted by applying Fick's Law for Bulk Gas Diffusion which was set forth earlier and indicated as equation (2).

The individual resistances of each of the layers of the diffusive material 21 to mass transfer were obtained from the overall apparent sampling rates by utilizing an analogy which draws a relationship between electrical resistance and diffusional resistance. This is discussed in greater detail in an article authored by E. D. Palmes and R. H. Lindenboom entitled "Ohm's Law, Fick's Law, and Diffusion Samplers for Gases," Analytical Chemistry 51, 2400–2401 (1979). In that article an equation was put forth which stated:

$$\text{Total Diffusional Resistance} \propto 1/S_{tot} = 1/S_{core} + 2/S_{membrane\ layers} \quad (3)$$

where $S_{tot}$, $S_{core}$, and $S_{membrane\ layers}$ are the sampling rates of laminated materials as a whole expressed in cubic centimeters per minute. This of course includes the porous plastic core 11 and microporous PTFE membrane layers 37, respectively. Using this formula, it was determined that the surface layers, that is the PTFE membrane 37, had a mass transfer resistance three times higher than that of the porous plastic core 11 even though they had a void volume equal to, and a combined thickness of only one tenth that of the porous plastic core.

Upon completion of these observations, it was subsequently determined that mass transfer through the diffusive material 21 having PTFE membranes 37 with a pore dimension of 0.02 microns was dominated by Knudsen diffusion, the subject diffusion being named after M. Knudsen who discovered this phenomena in 1909. As should be understood, Knudsen diffusion is a transport mechanism clearly distinguishable from bulk gas diffusion, that is, bulk gas diffusion applies when the cross-sectional dimensions of a diffusion channel are much smaller than the mean free path length of a gas molecule in a gas mixture. The means free path length is the average length a gas molecule must travel before colliding with another gas molecule. In the ambient atmosphere 36 the mean free path length is approximately $10^{-5}$ cm, and thus pores of 0.02 micrometers $(0.2 \times 10^{-5}$ cm) meet this criteria. Those skilled in the art will readily recognize that within a Knudsen diffusion channel the probability of a gas molecule colliding with another gas molecule is very small as compared to the probability that it will collide with the wall of the diffusion channel. Therefore the mass transfer of a gas contaminant through diffusive material dominated by Knudsen diffusion becomes dependent upon the collisions of individual gas contaminant molecules with the walls of the diffusion channel, and substantially independent of the collisions with one another or other gas molecules present in the gas mixture. Inasmuch as convective movement in the ambient atmosphere is propagated by means of intermolecular collisions, it should be readily recognized that mass transfer through a Knudsen diffusion channel is inherently resistant to the interference occasioned by convective air movements in the immediate vicinity thereof.

Although the pores in which the Knudsen diffusion mechanism occurs are small as compared to the mean free path length of the gas molecules, they are large as compared to the dimensions of the gas molecules themselves. Typically, the diametral dimensions of molecules with molecular weights of 300 or less, that is, those likely to have a measurable vapor pressure, lie in a range of between approximately 2 and 10 Angstroms (0.002 and $0.01 \times 10^{-5}$ cm.) It should be understood, therefore, that a well-defined theoretical framework has been derived from the kinetic theory of gases that describe the properties of diffusion which take place under Knudsen conditions. For example, the articles authored by E. A. Mason and A. P. Malinauskas (1983), entitled *Gas Transport in Porous Media: The Dusty-Gas Model*, Elsevier Science Publishing Company, Inc., New York, N.Y.; and the article authored by R. E. Cunningham and R. J. J. Wiliams (1980), entitled *Diffusion in Gases and Porous Media*, Plenum Press, New York, N.Y. discuss this subject. More particularly it has been empirically determined that the transport of a gas molecule through a capillary tube of circular cross-section with a given radius r is proportional to a Knudsen diffusion coefficient which is calculated by utilizing the formula:

$$D_{Kn} = [2r(8RT/\pi M)^{\frac{1}{2}}]/3 \qquad (4)$$

where $D_{kn}$ = the Knudsen diffusion coefficient expressed in square centimeters per minute (cm$^2$/min); r = the radius of the individual pores expressed in centimeters, (cm); R = the gas constant expressed in (gms-cm$^2$-mole-°K.); T = the temperature expressed in degrees Kelvin (°K.), and M = the molecular weight of the gas contaminant expressed in grams per mole. In practice, the Knudsen diffusion mechanism occurs in porous solids that frequently have a random structure that differs significantly from the relatively perfect dimensions of laboratory capillary tubes. Knudsen diffusion which occurs through such porous solids is described by an equation similar to, and containing terms found in, equations (1) and (2) which were discussed earlier.

The equation that describes the Knudsen diffusion mechanism which takes place through such porous solids is set forth below:

$$W = pD_{Kn}A(C_a - C_i)t/L\partial \qquad (5)$$

The ideal Knudsen diffusion coefficient derived from equation 4 is reduced by an empirical "tortuosity" factor $\partial$ which typically lies in a range between 3 and 7. It has been discovered that the values of an effective Knudsen diffusion constant are defined as the ratio of $D_{Kn}/\partial$ and have been found to lie in a range between 0.1 and 2 square centimeters per minute and are thus substantially intermediate in value as compared with the analogs constants which define bulk gas diffusion and permeation.

The results obtained from the testing of the variously dimensioned diffusive material 21 and which are set forth in TABLE 2 indicated that the diffusive material constructed from PTFE membranes having a pore size of approximately 0.02 microns, and in which Knudsen regime diffusion applied, appeared to satisfy the invention objectives of maintaining a constant rate of mass transfer while being exposed to a range of convective air movements and simultaneously retaining the liquid collection media without the need for secondary protection features. In order to determine whether the diffusive material could be fabricated in sufficiently large quantities while simultaneously retaining substantially uniform performance characteristics, approximately 100 square feet of diffusive material 21 was fabricated, and several hundred disks or pieces of diffusive material were cut out in random patterns. The disks were utilized in a set of experiments which endeavored to examine the amount of gas contaminant collected as a function of the air concentration of the same gas. The results of these experiments are summarized in TABLE 3.

TABLE 3

| (μg/L)min of Exposure (1) | Number of Dosimeters Exposed | Amount of Contaminant Collected, Expressed in micrograms | Relative Precision (2) |
|---|---|---|---|
| 34 | 20 | 0.42 | 4.4% |
| 71 | 20 | 0.89 | 5.1 |
| 143 | 20 | 1.66 | 5.7 |
| 205 | 20 | 2.50 | 6.2 |
| 334 | 20 | 3.81 | 3.2 |

(1) The test dosimeters were exposed to test atmospheres containing formaldehyde at concentrations ranging between 0.1 and 1 microgram per liter (approximately 0.1 to 1 ppm) for periods of approximately 4 hours.

(2) The relative precision is the standard deviation of the amount of contaminant collected expressed as a percentage of the mean.

The test results demonstrated that the entire lot of randomly shaped diffusive material allowed a selected gas contaminant to be collected with relatively excellent precision at a rate which was substantially linearly proportional to its air concentration. A least squares analysis applied to a plot of the micrograms of contaminant collected vs. the microgram-hours of exposure yielded a line having a slope of 11.3 mL/min, intercept 1.25 mL/min, and a correlation coefficient of 0.991.

In order to determine whether the gaseous contaminated dosimeter performance of the instant invention could be satisfactorily predicted on the basis of theory and a minimum amount of empirical data, a new series of experiments were conducted which endeavored to examine the relationship of the amount of gas contaminant collected as a function of the air concentration of that contaminant for a variety of different gases. Applying equation 4 noted above to the instant situation it should be expected that the rates of mass transfer for various gases through a selected Knudsen diffusive material should vary in proportion to the inverses of the square roots of their various molecular weights. The results of these experiments are summarized in TABLE 4, below:

TABLE 4

| Contaminant | M. Wt. | $1/(M. Wt.)^{\frac{1}{2}}$ | Observed Sampling Rate (1) | Calculated Sampling Rate (2) | Difference (2) |
| --- | --- | --- | --- | --- | --- |
| Formaldehyde (3) | 30 gms/Mol | 0.183 | 11.3 mL/min | 12.9 mL/min | −13.8% |
| Sulfur Dioxide (4) | 64 | 0.125 | 9.6 | 8.8 | +7.8 |
| Ammonia (5) | 17 | 0.243 | 18.1 | 17.1 | +6.0 |
| Water Vapor (6) | 18 | 0.236 | 16.3 | 16.6 | −1.7 |

(1) The observed sampling rates were obtained by exposing test dosimeters to a constant concentration of each contaminant for time periods spanning at least a fivefold range. The least squares analysis slope of a plot of amount collected vs (concentration × time) yields the sampling rate.
(2) A linear relationship between the sampling rate and the inverse of the square root of the molecular weight of the selected contaminant is predicted by equation (4). A least squares analysis of a plot of sampling rate vs. $1/(M. Wt.)^{\frac{1}{2}}$ was therefore performed and yielded a satisfactory result (slope = 77.0 [(Mol. Wt.)$^{\frac{1}{2}}$-mL/min], intercept = −1 [(Mol. Wt.)$^{\frac{1}{2}}$-mL/min], and correlation coefficient = 0.9318). The values of the least squares line were used to compute calculated sampling rates by substituting in known values of $1/(M. Wt.)^{\frac{1}{2}}$. The last column shows the percent difference between the sampling rate computed from the least squares line and the observed value.
(3) Formaldehyde was collected and analyzed as described in TABLE 2.
(4) Sulfur Dioxide was collected in an aqueous solution of buffered formaldehyde and analyzed using a modified West-Gaeke pararosaniline procedure.
(5) Ammonia was collected in an aqueous sulfuric acid solution and analyzed using a modified Nessler's Reagent procedure.
(6) Water vapor was collected by placing solid desicated molecular sieve in the dosimeter (inverted so that the molecular sieve was in contact with the diffusive material), and analyzed by computing the weight gain during the exposure period.

These test results clearly showed that performance date acquired with respect to the rate of mass transfer of one or more gases through a selected diffusive material can be utilized to predict the rate of mass transfer of a new gas through the same diffusive material.

The assorted test results indicated that a gaseous contaminant dosimeter having a Knudsen type diffusive material 21 would exhibit characteristics wherein mass uptake could be predicted to be proportional to the ambient concentration of the selected contaminant and would further be inherently independent of the convective gas movement over a practical range of values. Further the test results indicated that the diffusive material would inherently retain the aqueous or solid collection media 31 without secondary design features. Moreover it was clearly established that the diffusive material could be manufactured in sufficiently large quantities while maintaining uniform performance characteristics. As should be understood once the performance characteristics of a Knudsen type diffusive material is empirically determined for one or more contaminants, its performance characteristics with respect to other contaminants can be easily and satisfactorily predicted. Further by combining equation (4) with the known dependence of $C_a$ (and $C_i$ if applicable) the rate of mass transfer by a Knudsen type diffusion material can be shown to vary predictably with temperature and pressure as a function of $P/T^{\frac{1}{2}}$. Finally it has been determined that the response time can be shown by theory to be equal to the equation $L_2/6D_{Kn}$ and is typically rapid, as compared to the fluctuations in the gas contaminant concentration.

The diffusive material 21, as constructed from commercially available starting materials, and shown in FIG. 1, includes two PTFE membranes 37 having a 0.02 micron pore size, and a thickness of approximately 0.003 inches which are individually thermally bound to the opposite sides of a macroporous rigid core layer 11 of polyethylene having a thickness of approximately 0.0625 inches. Other materials of substitution will hereinafter be discussed in greater detail.

The physical characteristics that permits the diffusive material 21 to resist the deleterious effects of convective air movements is that Knudsen diffusion predominates in the PTFE membranes 37. To characterize the PTFE membrane structure, such as that shown in FIG. 4, manufacturers of same must specify the effective pore size 14 of the PTFE membrane material 37 be performing one or both of two tests which are set forth below. The first test is a bubble point test which was discussed earlier, wherein increasing pressure is applied to a wetted sample of PTFE membrane until the first steady continuous stream of bubbles appears. Using a semi-empirical formula the pressure at which bubbles first appear can be related to the maximum pore size present in the membrane. The manufacturer's literature utilizes the following formula:

$$P = 4K\sigma \cos(\phi)/d \qquad (6)$$

where P=the bubble point pressure; K=the shape correction factor; $\sigma$=the surface tension, $\phi$=the liquid-solid contact angle; and d=the pore diameter. The average pore size of the PTFE membrane is then estimated by assuming a normal distribution of pore sizes bounded at the upper end by the maximum pore size indicated by the bubble point test.

The second test which can be employed for purposes of selecting a PTFE membrane 37, which has a suitable pore size wherein Knudsen diffusion predominates is an air flow rate test. In the air flow rate test the rate at which air flows through a selected PTFE membrane 37, which has been subjected to a slight pressure gradient, is measured. As earlier discussed, the data for both tests are summarized in TABLE 1.

In order to select a suitable microporous PTFE membrane 37 for use in the present invention it should be understood that no amount of pressure can force bulk gas transport through a true Knudsen diffusion channel, therefore, with respect to the bubble point test noted above, a successful PTFE membrane is one which would resist bubble formation until pressures are reached that would physically disrupt or deform same. With respect to the data shown in TABLE 1 this disruption or deformation process occurs in the case of the 0.02 micrometer PTFE membrane at a water entry pressure of 350 pounds per square inch (PSI). Such test results indicate that even the upper bound pore sizes in the same PTFE membrane are highly resistant to bulk gas movement induced by a pressure gradient, and therefore can be expected to resist convective bulk gas movement. In order to select a suitable PTFE membrane utilizing the air flow rate test it should be understood that the air flow measurement takes place in the presence of a slight pressure drop. This flow of air is necessary to demonstrate that the PTFE membrane is porous and not solid. If the pressure drop of 4.88" of water, used as the test condition in TABLE 1, is expressed as a concentration gradient, (since one unit describing pressure is the number of molecules per unit volume), and a value for $D_{Kn,eff}=(pD_{Kn}/\partial)$ is obtained from the data shown in TABLE 4, then in that event the measured air flow is within a factor of two of that which would be computed assuming that the entire air flow was generated by Knudsen diffusion.

Having utilized the aforementioned criteria to identify suitable samples of PTFE membranes one should further note that the efficiency of mass transfer through a diffusive material in which Knudsen diffusion applies varies directly as the void volume and indirectly as to the thickness. Reported values for the former typically lie in a range for example between 0.1 (porous silica-alumina catalysts) and 0.5, that is PTFE membranes 37 as utilized in the instant invention with the preference being to employ materials with the highest available void volume to maximize mass transfer efficiency. As earlier indicated, Equation (5) may be used to compute the range of acceptable thicknesses for particular application, although parenthetically the preference would most often be to select the thinnest available material for purposes of achieving the highest rate of mass transfer. Further the preferred membrane material would be one which does not substantially react with, that is adsorb or absorb the gaseous components passing through it. In the present invention PTFE membranes 37 were selected as one of the most inert substances commercially available. Other porous materials which may be used as a "Knudsen diffusion" surface layer for regulating mass transfer include for example PVF which is otherwise known by the trademark Tedlar ®. This material theoretically could be manufactured with pore sizes in the Knudsen range. Further, mixed acetate and nitrate esters of cellulose can be obtained with a pore size of 0.025 micrometers and comparable physical specifications. The "Knudsen diffusion" surface, whatever its individual composition, must exhibit the property of hydrophobicity which would permit it to retain an aqueous collection medium 31 without further structural limitations. This is a highly desirable feature inasmuch as many methods which are recommended by recognized advisory agencies for the accurate and specific collection and measurement of selected gaseous contaminants involve collection of same in aqueous collection mediums 31. Examples include, but are not limited to, the various methods recommended by the American Public Health Association and the National Institute of Occupational Health and Safety for the determination of ammonia, acetaldehyde, acetic anhydride, amines, formic acid, hydrazine, hydrogen bromide, hydrogen chloride, hydrogen fluoride, hydrogen cyanide, hydrogen sulfide, chlorine, sulfur dioxide, nitrogen dioxide, and ozone. Further, one skilled in the art will readily recognize that it is possible to treat other surfaces so as to give them the trait of hydrophobicity. For example, one can treat mixed acetate and nitrate esters of cellulose with an application of silicon.

In the present invention an overall laminate type structure was selected in order to provide physical support for the selected membranes 37. Use of a support material 11 may or may not be necessary for other candidate Knudsen type membranes. If desired, other supporting or moderating type layers may be used in combination with the selected Knudsen type membranes to confer the desired properties. Porous support materials 11 which may be utilized include but are not limited to porous plastics such as polyethylene, polypropylene, polycarbonate, and polyurethane; or porous woven or fritted glasses; or sintered or other porous metals such as stainless steel. In an endeavor to limit the influence of such supports on mass transfer, they should be selected so as to have a minimum thickness required for their role, and a maximum porosity (void volume). As should be understood Equation (2) can be used to select appropriate candidate materials which can be substituted in the place of the porous support material 11.

The gaseous contaminant dosimeter 30 of the present invention utilizes a vial 20 which is manufactured of glass, in combination with a standard septum type cap 22 which secures a disk of diffusive material 21 in fluid impeding relation in the neck 33. Assembled from easily available materials, such a gaseous contaminant dosimeter is inexpensive and reusable. Further, the area of the diffusive material 21 exposed to the contaminant gas may be easily changed to modify the rate of collection if this is desirable. Moreover it should be readily recognized that glass is relatively inert, and can contain a wide variety of chemical reagents without inducing unproductive or interfering side reactions. Indeed, the methods referred to earlier and which are recommended by recognized advisory agencies for the accurate and specific measurement of gas contaminants utilizes a method that involves the placing of a collection medium 31 in a glass "bubbler" not shown, and drawing air having the gaseous contaminant to be detected through the collection medium by means of a pump also not shown. Further, organic gases are frequently collected by drawing air through a glass tube containing activated charcoal by means of a pump. For selected applications, other solid sorbents such as silica gel could be used.

The gaseous contaminant dosimeter of the instant invention also simplifies analysis procedures after the selected gaseous contaminants have been collected. For example, when a liquid collection media 31 is used, developing reagents can be added directly to the vial 20 thereby developing a color reaction. The gaseous contaminant concentration can then be determined by comparing the developed color to a comparison card or by inserting the device directly into the sample well of a colorimeter. Moreover with pre-packaged reagents an analysis of this sort can be conducted on the job site by relatively unskilled personnel. Alternatively, aliquots of liquid collection media may be withdrawn from the vial 20 for subsequent analysis by gas or liquid chromatography, spectroscopy, ion-specific electrochemistry or any of the analytical techniques commonly in use. When solid sorbents are employed desorbing solvents, such as carbon disulfides, can be added directly to the vial 20 and an aliquot of same can be subsequently withdrawn for latter analysis by employing gas or liquid chromatography or other desired means.

Therefore, it will be seen that the gaseous contaminant dosimeter apparatus of the instant invention is adapted to enhance the efficiency, speed, and accuracy with which the concentration of assorted gaseous contaminants can be determined in selected operational environments; provides a fully, dependable and practical means by which individual "breathing zone" measurements can be performed for selected personnel; and further is operable to retain both aqueous and solid sorbents with the attendant benefits associated therewith; the gaseous contaminant dosimeter device being of both sturdy and dependable construction and relatively inexpensive to manufacture and maintain.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

I claim:

1. A gaseous contaminant dosimeter apparatus for measuring the concentration of gaseous contaminants in a gas mixture, the apparatus comprising:
    a container having an opening formed therein;
    a diffusing material borne by the container and disposed in fluid impeding relation in the opening to isolate the interior of the container from an outside gas mixture, said diffusing material including a pair of microporous membranes which are individually laminated on the opposite sides of a macroporous support member, the microporous membranes permitting the passage of the gaseous contaminants into the container substantially by Knudsen regime diffusion; and
    a collection medium disposed in the container and operable to combine with the gaseous contaminants entering therein thereby facilitating the measurement of the gaseous contaminant concentration.

2. The apparatus of claim 2 wherein the microporous membranes each have a distribution of internal free passages with cross-sectional dimensions that are generally smaller than the mean free path length, and larger than the molecular sizes of selected gaseous contaminants in the gas mixture, and the microporous membranes are hydrophobic.

3. The apparatus of claim 2 wherein the microporous membranes are formed of a material in which the effective cross-sectional dimensions of the internal free passages of the material lie substantially in a range between $10^{-6}$ and $10^{-7}$ cm when the gas mixture containing the gaseous contaminants is air under ambient conditions.

4. The apparatus of claim 3 wherein the support member is a material having internal free passages with effective cross-sectional dimensions greater than the mean free path length of selected gaseous contaminants in the gas mixture.

5. The apparatus of claim 1 wherein the collection medium is a solid or liquid which is operable to adsorb, absorb, or react with selected gaseous contaminants, the amount of adsorption, absorption or reaction being utilized to determine the gaseous contaminant concentration.

6. The apparatus of claim 5 wherein the collection medium is an aqueous solution suitable for sorption of or reaction with selected gaseous contaminants and which further is compatible with selected measurement methods specific and quantitative for the measurement of said gaseous contaminants so collected.

7. A gaseous contaminant dosimeter apparatus for determining the amount of gaseous contaminants in a gas mixture and whereby the gas mixture is air and the selected gaseous contaminants are one of the group of benzene, alkyl benzenes, alkanes, alkenes, alkynes, chlorinated hydrocarbons or other organic compounds or combinations thereof, the apparatus comprising:
    a container having an opening formed therein, and defining an internal portion;
    a diffusing material mounted on the container and disposed in fluid impeding relation in the opening thereby isolating the internal portion of the container from the gas mixture, the diffusing material including at least one microporous membrane wherein the passage of said gaseous contaminants through the microporous membrane is substantially by Knudsen Regime diffusion; and
    a collection medium is received in the internal portion of the container and includes activated charcoal, silica gel or other material which adsorbs, absorbs or reacts with the aforementioned selected gaseous contaminants, the collection medium being compatible with measurement methods specific and quantitative for the measurement of said gaseous contaminants so collected.

8. A method of determining the concentration of a selected gas contaminant in a gas mixture during a predetermined time, comprising:
    providing a container defining a chamber and having an opening formed therein;
    forming a diffusion barrier by laminating opposite sides of a macroporous support member with an individual microporous membrane having an effective pore size of at least 0.02 micrometers, the diffusion barrier operable to regulate the mass transfer of the selected gaseous contaminant by Knudsen Regime diffusion;
    positioning the diffusion barrier in fluid impeding relation in the opening;
    depositing a collection medium in the chamber which is adapted to react with the selected gaseous contaminants, the collection medium being compatible with measuring methods specific and quantitative for the measurement of said gaseous contaminant; and
    exposing the diffusion barrier to the gas mixture for a predetermined period of time thereby permitting the collection medium to adsorb, absorb or react with the gaseous contaminant which diffuses through the diffusion barrier.

9. The method of claim 8 wherein the microporous membranes are hydrophobic; and the collection medium is an aqueous liquid received in the chamber and disposed in contact with said diffusion barrier while said selected gas is being collected.

* * * * *

UNITED STATES PATENT AND TRADEMARK OFFICE
CERTIFICATE OF CORRECTION

PATENT NO. : 4,790,857
DATED : December 13, 1988
INVENTOR(S) : Robert R. Miksch

It is certified that error appears in the above-identified patent and that said Letters Patent is hereby corrected as shown below:

Column 9, line 15, delete "means" and substitute ---mean---.

Column 10, line 24, delete "analogs" and substitute ---analogous---

Column 10, line 36, after media, insert ---31---.

Column 11, line 3, delete "0.991" and substitute ---0.9991---.

Column 12, line 18, delete "be" and substitute ---by---.

Column 15, line 51, delete "claim 2" and substitute ---claim 1---

Column 16, line 55, delete "measuring" and substitute ---measurement---.

Column 16, line 54, delete "contaminants" and substitute ---contaminant---.

Signed and Sealed this

Thirteenth Day of June, 1989

Attest:

DONALD J. QUIGG

Attesting Officer

Commissioner of Patents and Trademarks